US011911197B2

(12) United States Patent
Searing et al.

(10) Patent No.: US 11,911,197 B2
(45) Date of Patent: Feb. 27, 2024

(54) X-RAY SENSOR SYSTEM FOR INTRAORAL TOMOGRAPHY (71) Applicant: BAE Systems Imaging Solutions Inc., San Jose, CA (US)

(72) Inventors: Stanley K. Searing, San Jose, CA (US); Marc K. Thacher, San Diego, CA (US); Kwang Bo Cho, San Jose, CA (US); Hung T. Do, San Jose, CA (US); Stephen W. Mims, San Diego, CA (US); Bruce E. Willy, Watsonville, CA (US); Glen L. Collier, Morgan Hill, CA (US); Douglas W. Teeter, Scotts Valley, CA (US); George Y. Wang, San Jose, CA (US)

(73) Assignee: BAE Systems Imaging Solutions Inc., San Jose, CA (US)

( * ) Notice: Subject to any disclaimer, the term of this patent is extended or adjusted under 35 U.S.C. 154(b) by 45 days.

(21) Appl. No.: 17/550,856

(22) Filed: Dec. 14, 2021

(65) Prior Publication Data
US 2023/0181133 A1 Jun. 15, 2023

(51) Int. Cl.
A61B 6/14 (2006.01)
H04N 5/32 (2023.01)
(Continued)

(52) U.S. Cl.
CPC ............ *A61B 6/145* (2013.01); *A61B 6/4233* (2013.01); *A61B 6/54* (2013.01); *G01T 1/247* (2013.01); *H04N 5/32* (2013.01); *H04N 25/75* (2023.01)

(58) Field of Classification Search
CPC ......... A61B 6/145; A61B 6/4233; A61B 6/54; G01T 1/247; H04N 5/32; H04N 5/378
See application file for complete search history.

(56) References Cited

U.S. PATENT DOCUMENTS

2010/0102241 A1* 4/2010 Zeller .................. H04N 5/32
378/38
2012/0280131 A1* 11/2012 Spartiotis ............ H04N 5/32
250/366

(Continued)

FOREIGN PATENT DOCUMENTS

WO 2020086094 A1 4/2020

OTHER PUBLICATIONS

International Search Report, PCT/US22/52818, dated Feb. 17, 2023, 9 pages.

*Primary Examiner* — David P Porta
*Assistant Examiner* — Mamadou Faye
(74) *Attorney, Agent, or Firm* — Finch & Maloney PLLC; Gary McFaline (57) ABSTRACT Techniques are provided for x-ray sensing for intraoral tomography. A methodology implementing the techniques according to an embodiment includes detecting an x-ray pulse based on energy received at one or more pixels of a pixel array. The method also includes integrating the energy received at each of the pixels of the array of pixels, in response to the detection, wherein the energy received at each of the pixels is associated with the x-ray pulse. The method further includes multiplexing readouts of analog signals from the array of pixels into two or more parallel channels. The method further includes simultaneously converting (or otherwise in parallel) the analog signals of each of the channels into digital signals and storing the digital signals in memory as frames of data. The method may further include, for example, transmitting the frames of data from the memory, over a Universal Serial Bus, to an imaging system.

20 Claims, 9 Drawing Sheets (51) Int. Cl.
   *G01T 1/24*   (2006.01)
   *A61B 6/00*   (2006.01)
   *H04N 25/75*  (2023.01)

(56) References Cited

U.S. PATENT DOCUMENTS

2014/0016748 A1* 1/2014 Spahn ............... G01T 1/247
                                              250/370.08
2017/0049410 A1* 2/2017 Zeller ............... A61B 6/4233
2020/0345318 A1  11/2020 Turner et al.
2021/0353238 A1* 11/2021 Zhou ................ A61B 6/4417

* cited by examiner

X-RAY SENSOR SYSTEM FOR INTRAORAL TOMOGRAPHY

FIELD OF DISCLOSURE

The present disclosure relates to x-ray sensor systems, and more particularly, to x-ray sensor systems for intraoral tomography.

BACKGROUND

X-ray imaging is frequently used in dental care to visualize features of tooth anatomy, for example cavities or other defects that require attention and treatment. Originally, film was used to capture images generated by the relative attenuation of the x-ray radiation as it passed through different parts of the tooth. Later, electronic sensors came into use as a replacement for film and offered many advantages including faster access to the images (since the film development process was eliminated) and generally lower levels of radiation. Whether using film or an electronic sensor, however, the result is a single 2-dimensional image of the tooth (or teeth) in the field of view of the x-ray beam.

Although the following Detailed Description will proceed with reference being made to illustrative embodiments, many alternatives, modifications, and variations thereof will be apparent to those skilled in the art.

DETAILED DESCRIPTION

Techniques are provided for implementing an x-ray sensor system that is capable of capturing multiple dental x-ray images, at varying angles, and at a high enough acquisition rate to enable intraoral tomography. As noted previously, existing dental x-ray imaging techniques produce 2-dimensional images. These images lack the detail and improved diagnostic capabilities that may be achieved with 3-dimensional images that can be generated through tomographic processing of a sequence of 2-dimensional images from varying angles. In addition, there is currently no sensor that is fast enough, in terms of acquisition and reset time, and that can fit into a patient's mouth, allowing for a series of high resolution intraoral x rays images, to provide a tomographic dataset. To this end, and in accordance with an embodiment of the present disclosure, an x-ray sensor system is disclosed which provides a relatively high image acquisition and transfer rate such that a sufficient number of 2-dimensional x-ray images can be collected to generate a 3-dimensional tomographic image data set. The system is compact and anatomically shaped such that it may fit within a patient's oral cavity.

The disclosed techniques can be implemented, for example, in a gate-level logic device, a microprocessor, an embedded processor, or a software product executable or otherwise controllable by such systems, although other embodiments will be apparent in light of this disclosure. In accordance with an embodiment, a methodology to implement these techniques includes integrating energy received at each of one or more pixels of an array of pixels, in response to a trigger, wherein the energy received at each of the one or more pixels is associated with the x-ray pulse. In some embodiments, the trigger is provided by a tomographic imaging system to which the 2-dimensional x-ray images will be sent. In some other embodiments, the trigger is generated by detecting the x-ray pulse based on the energy received at the one or more pixels of the array of pixels. The method further includes multiplexing readouts of analog signals from the array of pixels into two or more parallel channels to increase acquisition speed. The method further includes performing parallel conversion of the analog signals of the channels into digital signals and storing the digital signals in memory onboard the sensor system as frames of data. The method further includes transmitting the frames of data from the memory, over a communications path, such as a Universal Serial Bus (USB), to the imaging system.

It will be appreciated that the disclosed techniques for sensor based image data capture, employing parallel data channels for faster acquisition and storage of pixel data, as described herein, may provide improved dental imaging and diagnostic capability, compared to existing techniques that generate only 2-dimensional images. The techniques disclosed herein may further be implemented in hardware or software or a combination thereof. Numerous embodiments and applications will be apparent in light of this disclosure.

Figure 1:
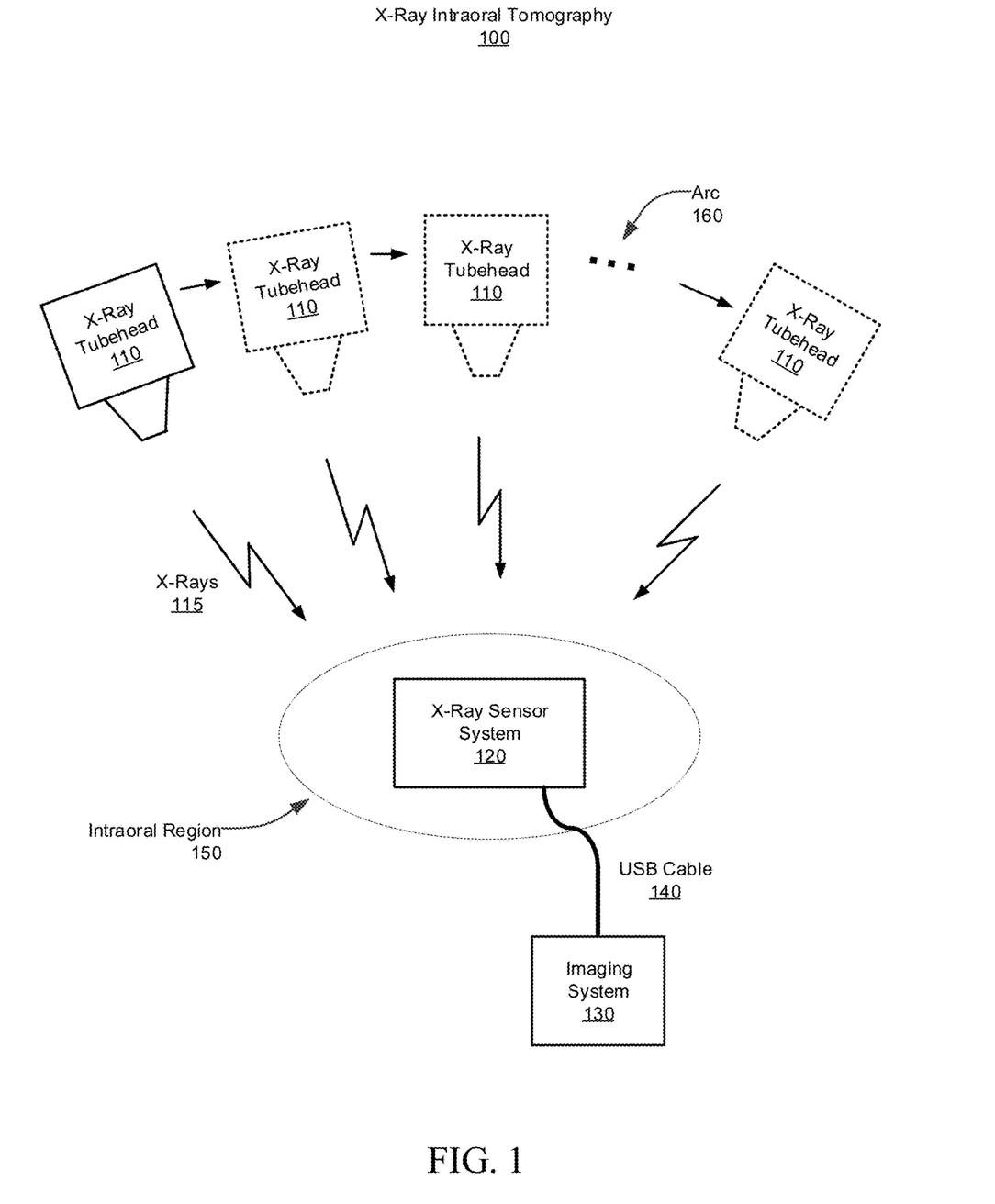
FIG. 1 illustrates an implementation of an x-ray sensor system for intraoral tomography, in accordance with an embodiment of the present disclosure.

FIG. 1 illustrates an implementation 100 of an x-ray sensor system 120 for intraoral tomography, in accordance with an embodiment of the present disclosure. An x-ray tubehead 110 generates x-rays 115 which are directed to the intraoral region of interest 150, for example the mouth of a patient undergoing dental imaging. The x-ray sensor system 120 is located in the intraoral region, for example behind a tooth being imaged, such that the x-rays 115 pass from the tubehead 110, through the tooth, before illuminating the sensor system 120. The sensor system then forms an image which is transmitted to an imaging system 130 which collects the images and performs tomographic processing to generate a 3-dimensional image. In some embodiments, the transmission may be over a cable, such as USB cable 140, which runs out of the patient's mouth, although other communications schemes are possible, including wireless communications.

In operation, the tubehead 110 travels through an arc 160 as shown and generates multiple x-ray pulses over the course of that range of travel. Each x-ray pulse may therefore illuminate the tooth from a different angle. For example, in some embodiments, 30 pulses are generated over 3 seconds of travel through a 360 degree arc. The x-ray sensor system 120 is configured to generate a 2-dimensional image for each x-ray pulse, as will be described below. The imaging system 130 is configured to collect and tomographically combine the 2-dimensional images to generate a 3-dimensional image of the tooth that can provide greater diagnostic information to the dental practitioner than would otherwise be available from individual 2-dimensional images.

Figure 2:
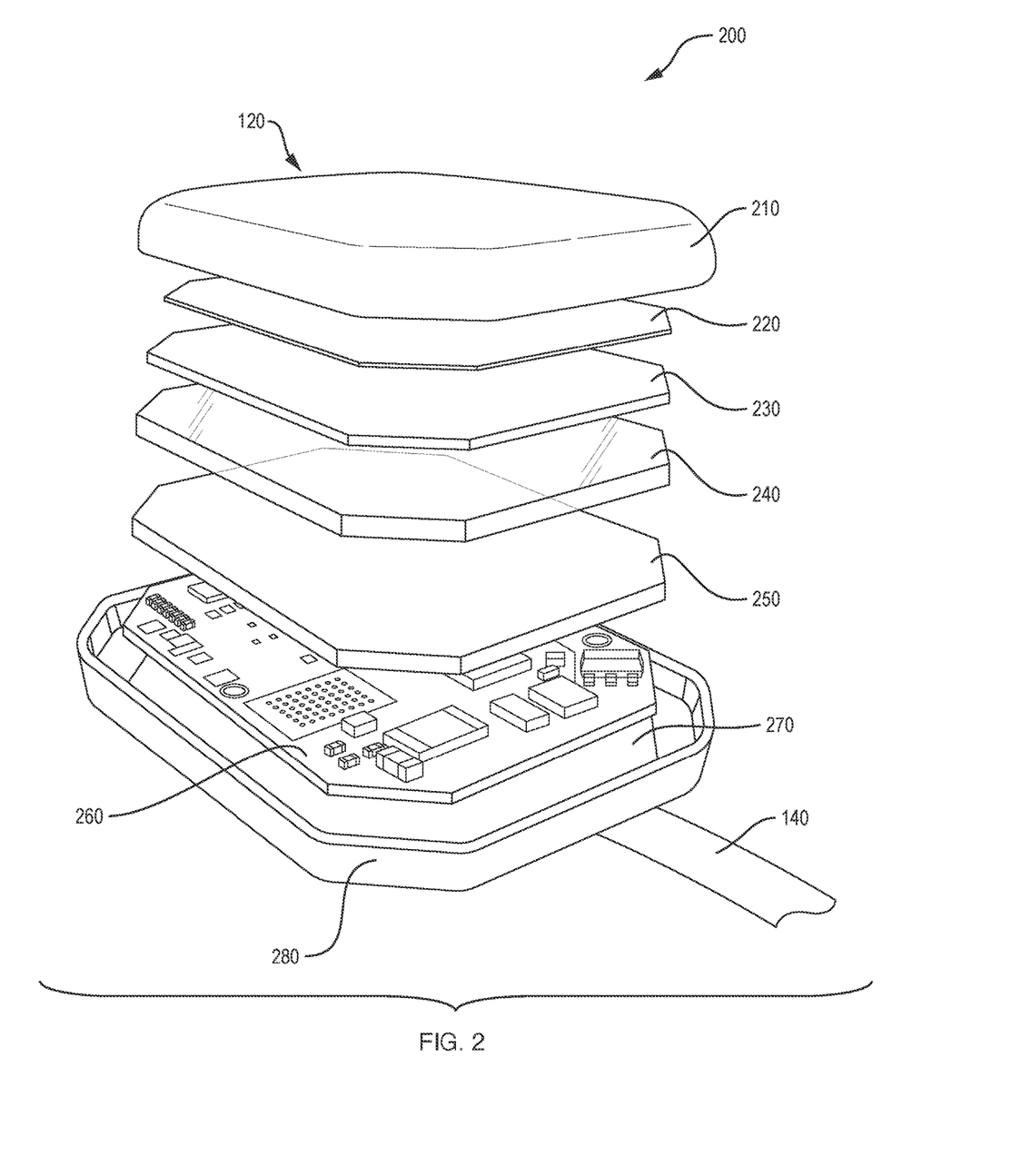
FIG. 2 is an exploded view of an example implementation of the x-ray sensor system of FIG. 1, configured in accordance with an embodiment of the present disclosure.

FIG. 2 is an exploded view 200 of the x-ray sensor system 120 of FIG. 1, configured in accordance with an embodiment of the present disclosure. The x-ray sensor system 120 is shown to comprise a number of layers including a buffer pad 220, a Cesium Iodide layer 230, a fiber optic plate 240, a Complementary Metal Oxide Semiconductor (CMOS) sensor die 250, a circuit board 260, and a metallization layer 270. The layers are enclosed in a capsule comprising a front, x-ray facing, portion 210, and a rear portion 280. The capsule provides a sealed and hygienic housing for the components/layers that is suitable for use as a dental intraoral device. Additional layers (not shown) may be included in some embodiments, for any suitable purpose.

The buffer pad 220 is configured to protect the Cesium Iodide layer, which is relatively fragile, and may also absorb stray light that reflects off the metallization layer. In some embodiments, the buffer pad may be fabricated as a layer of silicone, although any number of protective materials can be used (e.g., foam or plastic).

The Cesium Iodide layer 230 is configured to generate a fluorescent glow at a strength that depends on the level of x-ray illumination. In other words, a location on the Cesium Iodide layer that receives more x-ray radiation will glow more brightly than an area that receives less x-ray radiation. When the x-ray radiation passes through a tooth, the strength of the fluorescent glow will indicate the density of the tooth at that location (e.g., along the ray path of that portion of the x-ray). The Cesium Iodide layer 230 is a chemical coating that is disposed over the fiber optic plate 240. In addition to acting as a structural layer to support the Cesium Iodide, the fiber optic plate 240 also absorbs the x-ray radiation which protects the CMOS sensor die 250 and the circuit board 260 from damage.

The CMOS sensor die 250 comprises an array of photo diode circuits and is configured to detect the fluorescent glow generated by the Cesium Iodide layer 230. In some embodiments, each photo diode circuit generates an analog signal that may be associated with a pixel of the resultant x-ray image.

The circuit board 260 is configured to receive, process, store, and transmit the signals provided by the CMOS sensor die 250. Further details of sensor die 250 and circuit board 260 are discussed with respect to FIGS. 3 through 9. In particular, sensor die 250 may include pixel array 500 (FIG. 5) of sensor 300 (FIG. 3), and circuit board 260 may include ADC 310, system controller 320, memory 330, and USB controller 340 (FIG. 3).

The metallization layer 270, which may include a layer of lead, is configured to provide radiation protection as a safety measure to prevent stray x-ray radiation from reaching the patient.

The x-ray sensor system 120 also includes a communication cable 140, which may be a USB cable in some embodiments, and is configured to provide collected x-ray sensor data to an imaging system 130.

Figure 3:
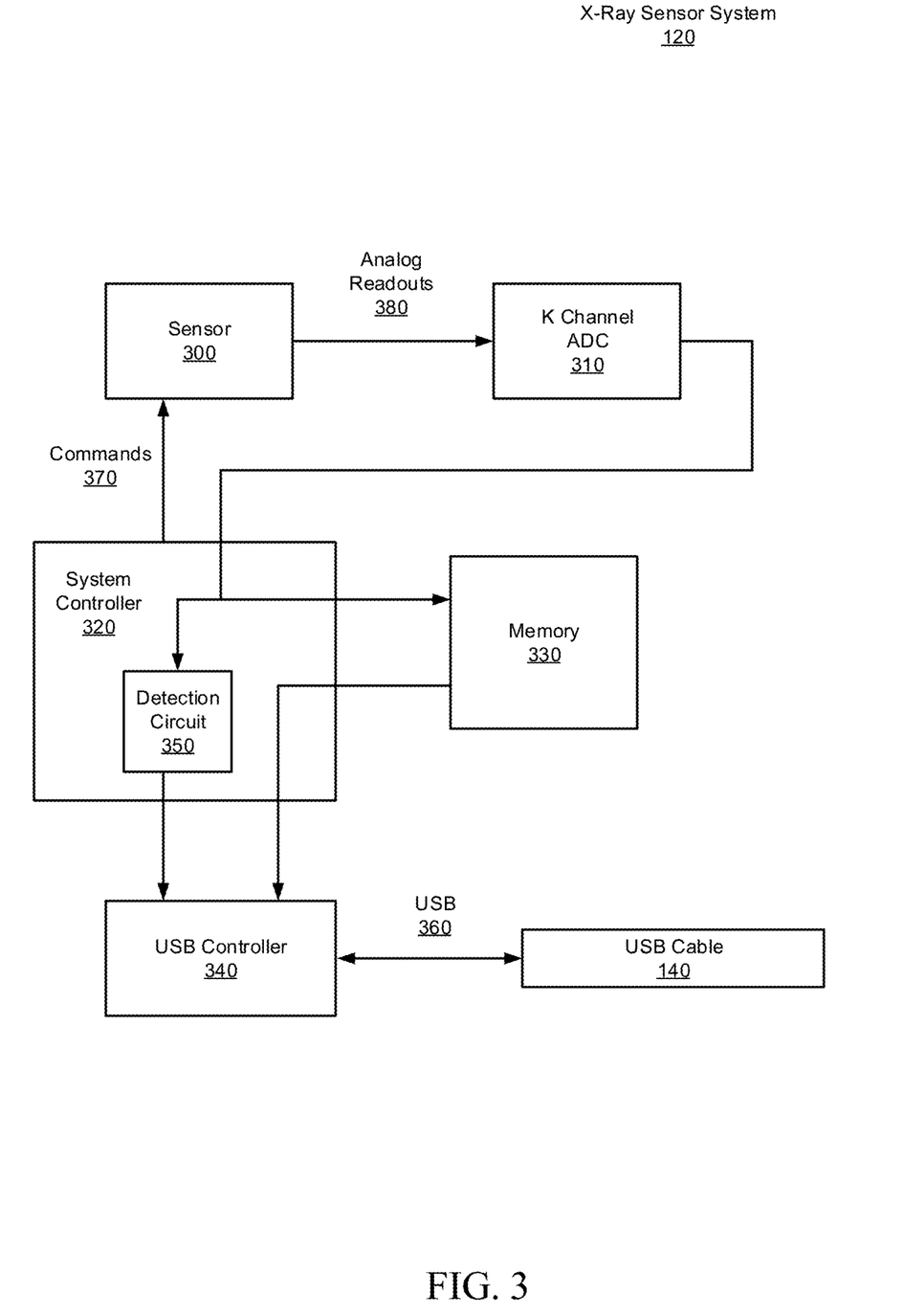
FIG. 3 is a block diagram of the x-ray sensor system of FIG. 1 and shows further details of the CMOS sensor die and circuit board of FIG. 2, configured in accordance with an embodiment of the present disclosure.

FIG. 3 is a block diagram of the x-ray sensor system 120 of FIG. 1, configured in accordance with an embodiment of the present disclosure. The x-ray sensor system 120 is shown to include a sensor 300, a multichannel analog to digital converter (ADC) 310, a system controller 320, which includes x-ray pulse detection circuit 350, a memory 330, and a USB Controller 340.

The sensor 300 comprises an array of pixel circuits arranged in rows and columns (e.g., M×N). In some embodiments, M=1850 and N=1344. Each pixel circuit includes a photo diode and is associated with a pixel of the resulting x-ray image. The sensor 300 which will be described in greater detail below, but at a high level sensor 300 is configured to capture energy associated with an x-ray pulse and provide an analog signal readout 380 of the energy from each pixel into multiplexed parallel channels (e.g., K channels).

The multichannel ADC 310 is configured to simultaneously convert, or otherwise perform parallel conversion of, the analog signals 380 of the K channels into digital signals. Thus, each analog signal 380 is received by a corresponding one of the channels of the multichannel ADC, according to some embodiments. In such a case, K analog signals 380 can be simultaneously converted to their digital equivalents. Note that, as used herein, simultaneous conversion is intended to include any form of contemporaneous or parallel conversion and is not intended to be limited to precise start and stop times for the conversion of each channel. Rather, the conversion of a given channel may overlap with the conversion of the other channels, but some of the channels may finish conversion before other channels finish; likewise, some of the channels may commence conversion before other channels commence. So long as there is contemporaneous overlap of the conversion, that conversion may be considered to be simultaneous or parallel conversion.

The system controller 320 is configured to generate commands 370 to the sensor 300 to clear the sensor 300 of data from a previous x-ray pulse, start and stop data collection on a new x-ray pulse, and adjust the gain setting of the sensor photodiodes. The system controller 320 is also configured to control data transfer from the ADC to memory 330, to control data transfer from the ADC to the pulse detection circuit 350, and to control data transfer from the memory 330 to the USB controller 340.

In some embodiments, the detection circuit 350 is configured to detect the beginning of a new x-ray pulse, based on a sampling of groups of pixels in pre-selected rows of the pixel array, as will be described in greater detail below in connection with FIG. 7. The detection circuit 350 is also configured to generate a data collection trigger in response to that detection, the trigger causing system controller 320 to issue a command to the sensor 300 to start data collection. Data collection may subsequently be stopped after a predefined period of time has elapsed, for example based on a known duration of the x-ray pulses. In some other embodiments, the data collection trigger is provided by the imaging system 130. The imaging system controls the start and stop of x-ray pulse generation and can therefore direct the sensor system to initiate data collection. In these embodiments, the detection circuit is not required.

The USB Controller 340 is configured to transmit the frames of data from the memory 330 to the imaging system 130, for example over the USB bus 360.

Figure 4:
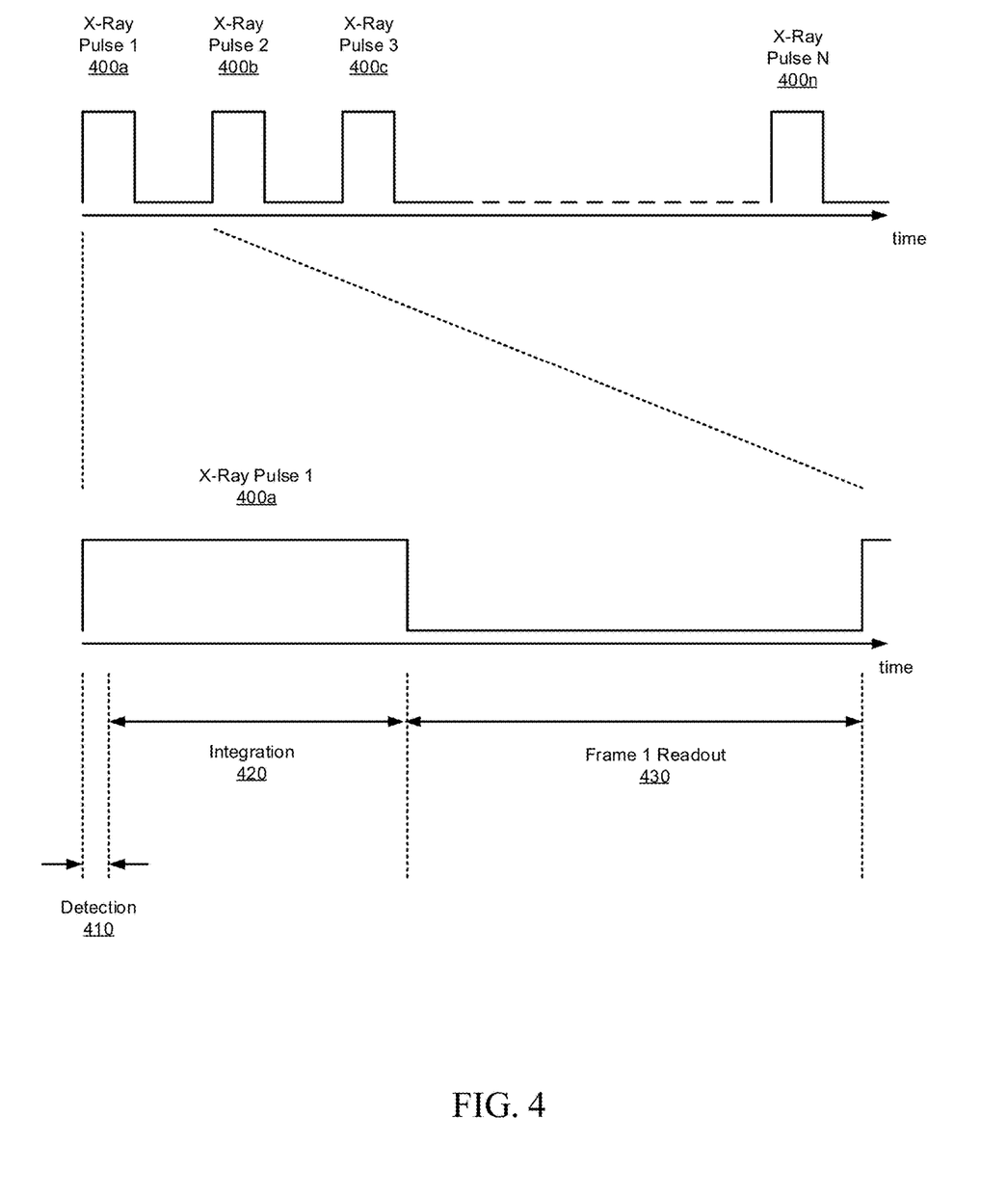
FIG. 4 is a timing diagram of the operation of the x-ray sensor system of FIGS. 2 and 3, in accordance with an embodiment of the present disclosure.

FIG. 4 is a timing diagram of the operation of the x-ray sensor system 120, in accordance with an embodiment of the present disclosure. A series of x-ray pulses 400a through 400n are shown along the top timeline. In some embodiments, 30 pulses are generated and received over a course of 3 seconds, which is to say that 10 pulses per second are processed by the sensor system 120 and that up to 30 images may be stored in memory prior to transmission from the sensor to the imaging system. In some embodiments, an image may be associated with multiple pulses.

An expanded view of the first pulse is shown on the bottom timeline. Detection of the first x-ray pulse occurs during a first time period 410. The sensor pixel array then integrates the x-ray energy received over the remaining duration of the x-ray pulse during the integration time period 420. Integration is associated with a buildup of charge received at a photo diode of each pixel of the pixel array, as described below. A frame of data is then read out from the sensor during the readout time period 430 for frame 1 (associated with the first x-ray pulse 400a). The process then repeats for each subsequent x-ray pulse. In some embodiments, the detection time period 410 may be approximately one millisecond (msec), the integration time period 420 may be approximately 32 msec, and the frame readout time period 430 may be approximately 67 msec.

Figure 5:
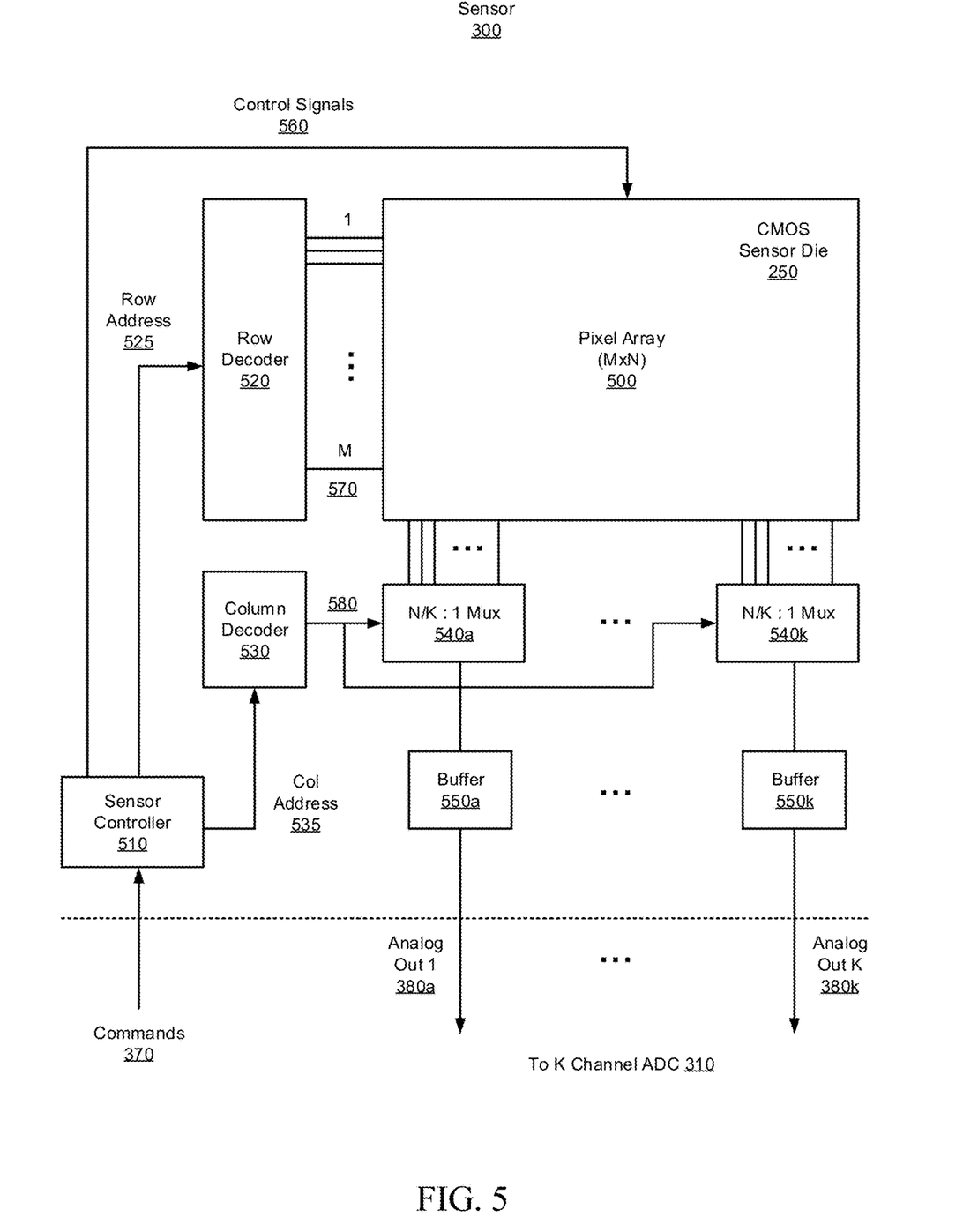
FIG. 5 is a block diagram of the sensor of the x-ray sensor system of FIGS. 2 and 3, configured in accordance with an embodiment of the present disclosure.

FIG. 5 is a block diagram of the sensor 300 of the x-ray sensor system of FIG. 3, configured in accordance with an embodiment of the present disclosure. The sensor 300 is shown to include a pixel array 500, a sensor controller 510, a row decoder 520, a column decoder 530, multiplexer circuits 540, and buffer circuits 550.

Pixel array 500 is implemented on the CMOS sensor die 250 and comprises an array of pixel circuits laid out in a pattern of M rows by N columns. Each of the pixels in the pixel array 500 comprises a pixel circuit that includes a photodiode that is configured to integrate the received fluorescent energy within the area of that pixel over the duration of the x-ray pulse, as will be described in greater detail below.

Sensor controller 510 is configured to receive commands 370 from the system controller 320 and control operation of the sensor based on those commands. For example, sensor controller 510 is configured to generate row addresses 525 and column addresses 535 to provide for readout of selected pixel circuits. Sensor controller 510 is also configured to generate control signals 560 for the pixel circuits, for example, to reset/clear the pixel, begin a new integration, and adjust the gain.

Row decoder 520 is configured to translate the row address 525 into one of M row selection signals 570. So, for example, if the row address 525 is set to one, the first row will be addressed, and if the row address 525 is set to M, the last row will be addressed.

Column decoder 530 is configured to translate the column address 535 into multiplexer control signals 580 to be provided to the K multiplexer circuits 540. The multiplexer circuits 540 are each configured to select one out of N/K columns based on the multiplexer control signals 580. So, for example, if the column address 535 is set to zero, the first multiplexer 540a will select the first column for readout, the second multiplexer 540b will select column N/K+1, the third multiplexer 540c will select column 2N/K+1, and so on. Similarly, if the column address 535 is set to two, the first multiplexer 540a will select the second column, the second multiplexer 540b will select column N/K+2, the third multiplexer 540c will select column 2N/K+2, and so on.

Thus, the combination of a row address and a column address will enable K pixels to be read out of the pixel array at the specified row at column spacings of N/K intervals starting at the specified column.

Buffer circuits 550 are configured to buffer (e.g., increase drive capability or strength) the K analog pixel values that are readout out of the pixel array, for transmission to the K channel ADC 310 of the x-ray sensor system 120.

Figure 6:
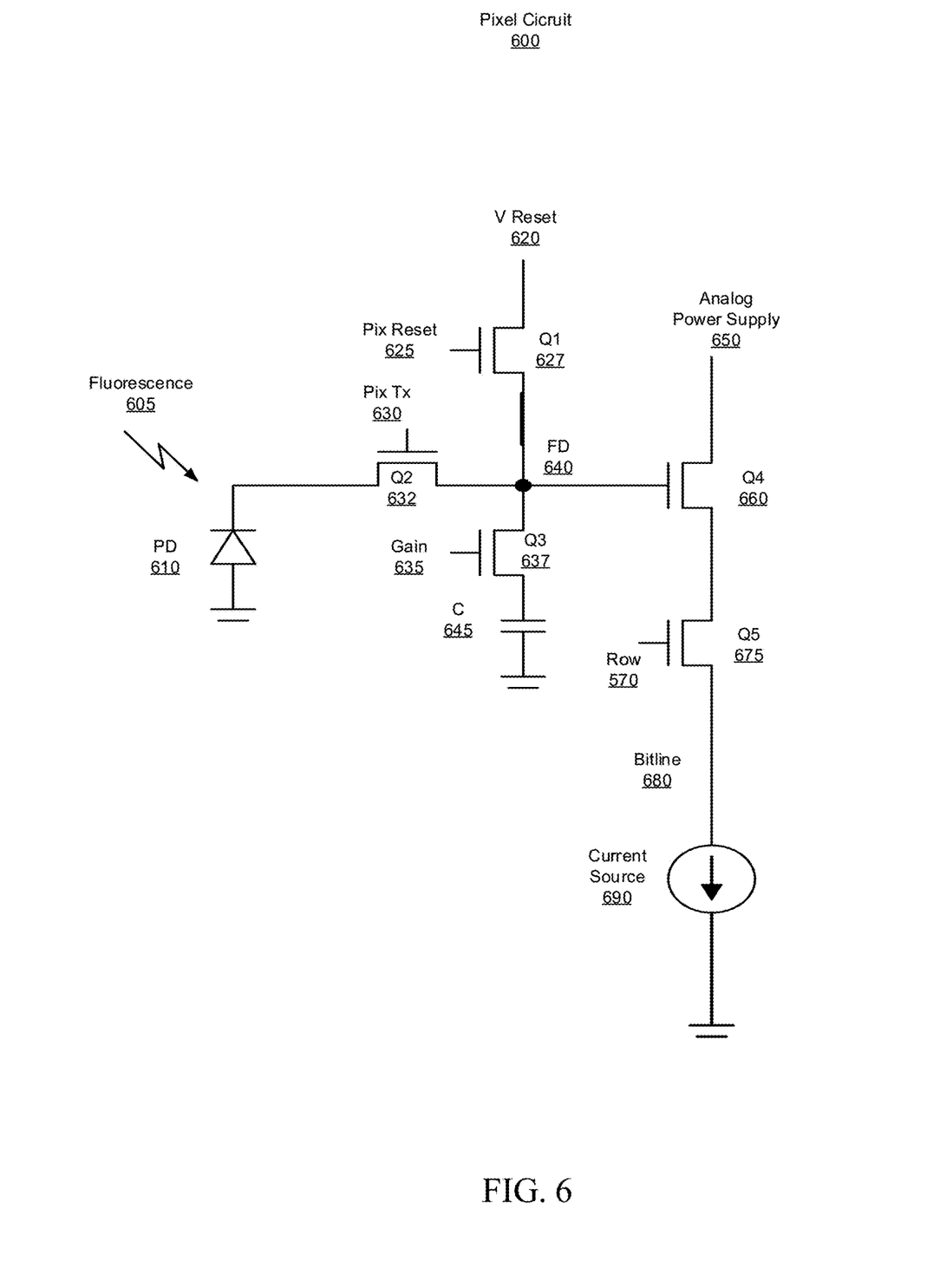
FIG. 6 is a schematic diagram of a pixel circuit of the pixel array (sensor) of FIGS. 2, 3 and 5, configured in accordance with an embodiment of the present disclosure.

FIG. 6 is a schematic diagram of a pixel circuit 600 of the sensor of FIG. 5, configured in accordance with an embodiment of the present disclosure. The pixel circuit 600 is shown to include a photo diode 610, a pixel reset transistor Q1 627, a pixel transmit transistor Q2 632, a gain switch transistor Q3 637, a gain capacitor C 645, an analog power supply 650, a source follower transistor Q4 660, a row control transistor Q5 675, and a current source 690.

Photodiode 610 is configured to detect the fluorescent glow emitted by the Cesium Iodide layer 230 in response to radiation from an x-ray pulse.

Pixel transmit transistor Q2 632 is configured to transmit the accumulated photo-charge from the photodiode 610 to the floating diffusion (FD) node 640 when the transistor Q2 632 is switched on (e.g., pixel transmit signal 630 is high). Pixel transmit signal 630 serves to initiate integration of the received energy at the pixel.

Pixel reset transistor Q1 627 is configured to reset the FD node 640 to a reset voltage 620 when the transistor Q1 627 is switched on (e.g., pixel reset signal 625 is high). Pixel reset signal 625 serves to clear the pixel, for example after readout is complete and prior to the next x-ray pulse.

Gain switch transistor Q3 637 is configured to toggle the pixel between a high gain mode and a low gain mode. When the pixel gain signal 635 is low, the capacitance at the FD node 640 is relatively small and the pixel has a relatively higher conversion gain, causing it to be more sensitive. When the pixel gain signal 635 is high, capacitor C 645 is switched into the circuit and the resulting capacitance at the FD node 640 is relatively large so that the pixel has a relatively lower conversion gain, causing it to be less sensitive, but with a higher full well capacity. The appropriate gain setting may be selected based on requirements for a particular application.

Source follower transistor Q4 660 and current source 690 are configured to generate an output voltage indicative of the potential on the FD node 640. Row control transistor Q5 675 is configured to provide the output of source follower transistor Q4 660 as a bit line 680 of the pixel array in response to the row selection signal 570 provided by the row decoder 520.

In some embodiments, the pixel reset signal 625, pixel transmit signal, and pixel gain signal 635 are included in the control signals 560 provided by sensor controller 510.

Figure 7:
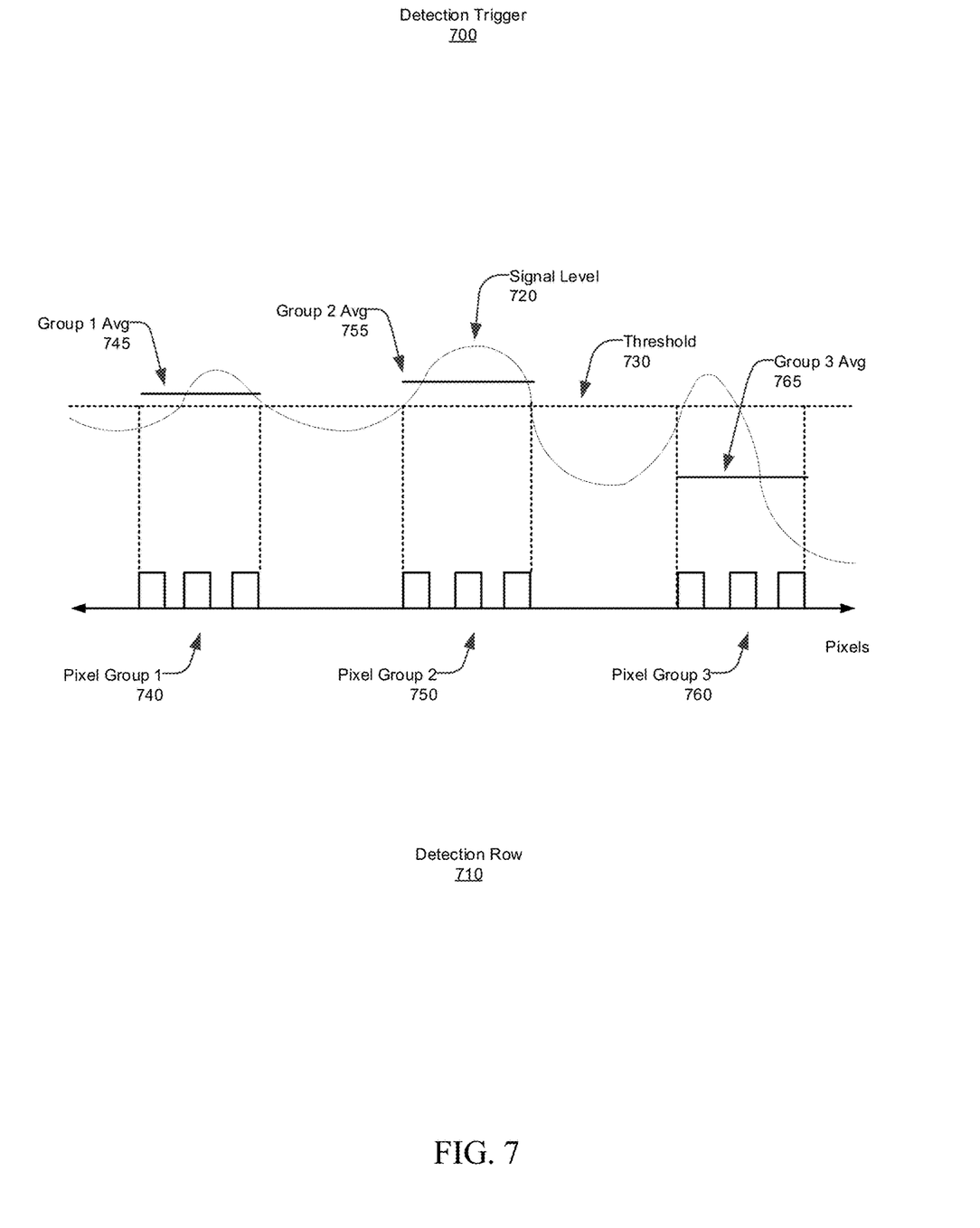
FIG. 7 illustrates x-ray detection triggering, in accordance with an embodiment of the present disclosure.

FIG. 7 illustrates x-ray detection triggering 700, in accordance with an embodiment of the present disclosure. As previously noted, the detection circuit 350 is configured to detect the beginning of a new x-ray pulse, based on a sampling of groups of pixels in pre-selected rows of the pixel array. In some embodiments, the number of pre-selected rows to be used for detection is six, and they may be spaced apart from each other by one or more non-detection rows. In some embodiments, the spacing between pre-selected rows may be constant (e.g., regular spacing), while in other embodiments the spacing may vary (e.g., irregular spacing). Some advantages of irregular spacing of the pre-selected rows include optimizing the spacing for faster access and/or biasing the detection towards a central region of the sensor.

In some embodiments, the process proceeds as follows. The pixels in each of the pre-selected detection rows are divided into groups, for example groups of 32 pixels. Then, starting with the first detection row and the first group, the received energy is summed (or averaged) over all of the pixels in that group. If the summed energy exceeds an energy level threshold, a count (which was initialized to zero) is incremented. Note that the energy level of some pixels in the group can be below the threshold and the group total (or average) can still exceed the threshold. The process continues with the second group and subsequent groups of the first detection row, and then continues onto the next detection row, etc. Whenever the summed energy exceeds the energy level threshold, the count is incremented. If, at some point, the count exceeds a threshold count value, a detection trigger is generated, and the detection process stops (and integration begins). In some embodiments, the threshold count value is three. If, after processing all of the detection rows, the count does not exceed the threshold count value, the process begins again at the first detection row and continues until a detection occurs.

FIG. 7 illustrates one of the pre-selected detection rows 710. A received signal energy level 720 is shown for that row, which varies from pixel to pixel (since the density of the tooth varies spatially). The energy level threshold 730 is also shown. Three pixel groups 740, 750, and 760 are also shown, along with the average of the pixel energy values in that group, 745, 755, and 765 respectively. In this example, the group 1 average 745 and the group 2 average 755 exceed the threshold, but the group 3 average 765 does not. So, in this example, the count for this row 710 would be two, since two pixel groups have an average above the threshold.

Methodology

Figure 8:
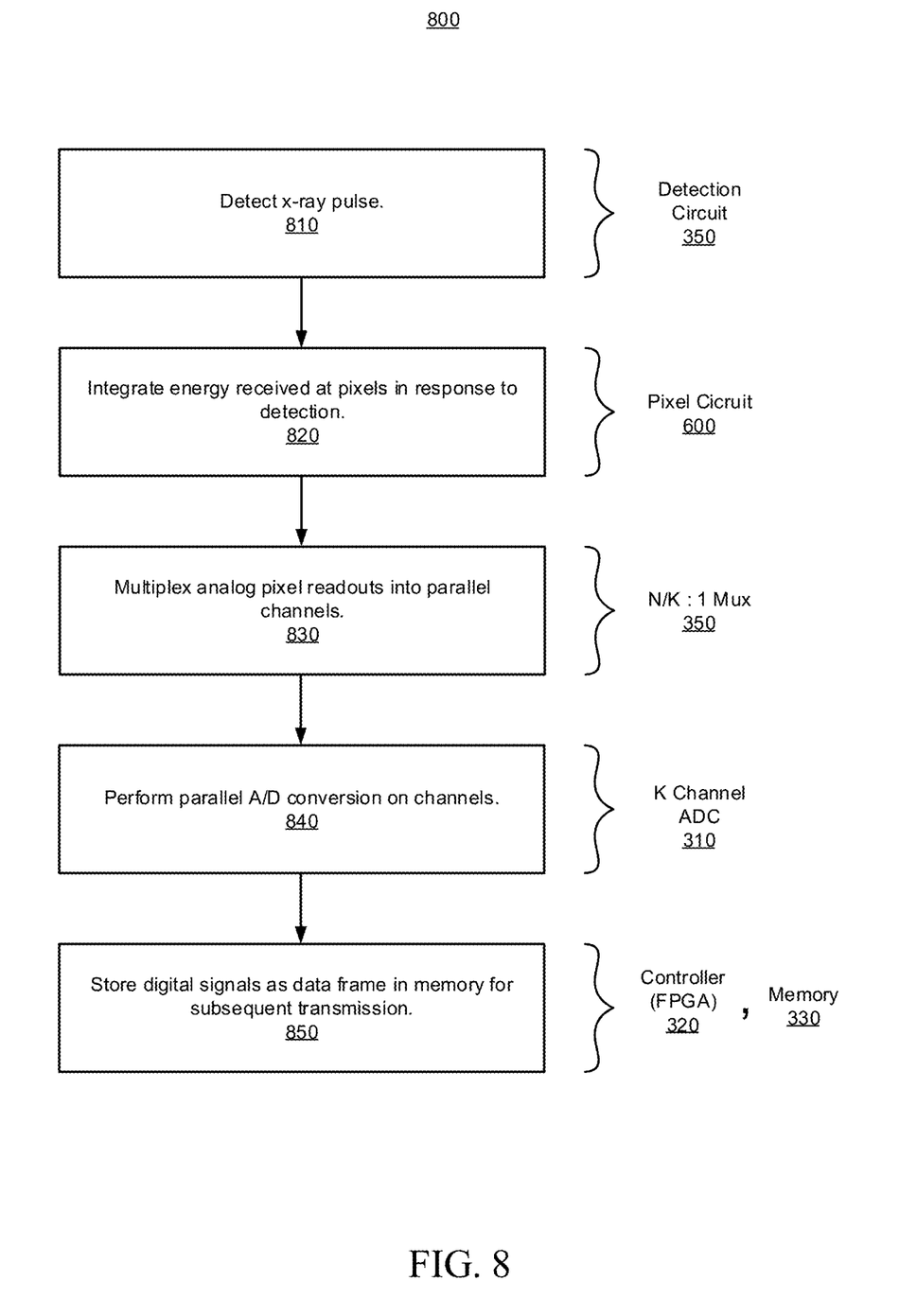
FIG. 8 is a flowchart illustrating a methodology for operation of the x-ray sensor system, in accordance with an embodiment of the present disclosure.

FIG. 8 is a flowchart illustrating a methodology 800 for operation of the x-ray sensor system, in accordance with an embodiment of the present disclosure. As can be seen, the example method includes a number of phases and sub-processes, the sequence of which may vary from one embodiment to another. However, when considered in the aggregate, these phases and sub-processes form a process for x-ray sensing for intraoral tomographic applications, in accordance with certain of the embodiments disclosed herein. These embodiments can be implemented, for example using the system architecture illustrated in FIGS. 1-7, as described above. However other system architectures can be used in other embodiments, as will be apparent in light of this disclosure. To this end, the correlation of the various functions shown in FIG. 8 to the specific components illustrated in FIGS. 1-7, is not intended to imply any structural and/or use limitations. Rather other embodiments may include, for example, varying degrees of integration wherein multiple functionalities are effectively performed by one system. Numerous variations and alternative configurations will be apparent in light of this disclosure.

As illustrated in FIG. 8, in one embodiment method 800 commences, at operation 810, by detecting an x-ray pulse based on energy received at each pixel of an array of pixels. In some embodiments, the detection is based on energy received, at a pre-selected subset of pixels, exceeding a threshold level. The pre-selected subset of pixels may comprise groups of pixels that are distributed over different rows of the array of pixels. In some embodiments, the detection may be triggered when the number of groups of pixels, for which the energy exceeds the threshold energy level, exceeds a threshold count value. In some other embodiments, as an alternative to x-ray pulse detection, a data collection trigger is provided by the imaging system 130.

Next, at operation 820, in response to the detection (or the trigger from the imaging system 130), the energy associated with the x-ray pulse that is received at each of the pixels is integrated over the time duration of the pulse.

At operation 830, readout of analog signals from the array of pixels is multiplexed into two or more parallel channels. At operation 840, the analog signals of each of the channels are converted by parallel ADCs (one for each channel) into digital signals.

At operation 850, the digital signals are stored in memory as frames of data for subsequent transmission. In some embodiments, the frames of data are read out of memory and transmitted over USB to an imaging system, for example a 3-dimensional or tomographic imaging system. In some embodiments, the frames are padded to a multiple of 512 bytes and transmitted as a USB burst transfer.

Of course, in some embodiments, additional operations may be performed, as previously described in connection with the system. These additional operations may include, for example, repeating the process for subsequent second x-ray pulses such that data frames collected from a first x-ray pulse are transmitted in parallel with the processing of a second x-ray pulse, to at least some extent of overlap. In some embodiments, the sensor system includes eight parallel channels and ADCs and the system is configured to store 30 frames of data in a time period in the range of 1 to 4 seconds.

Example Systems

Figure 9:
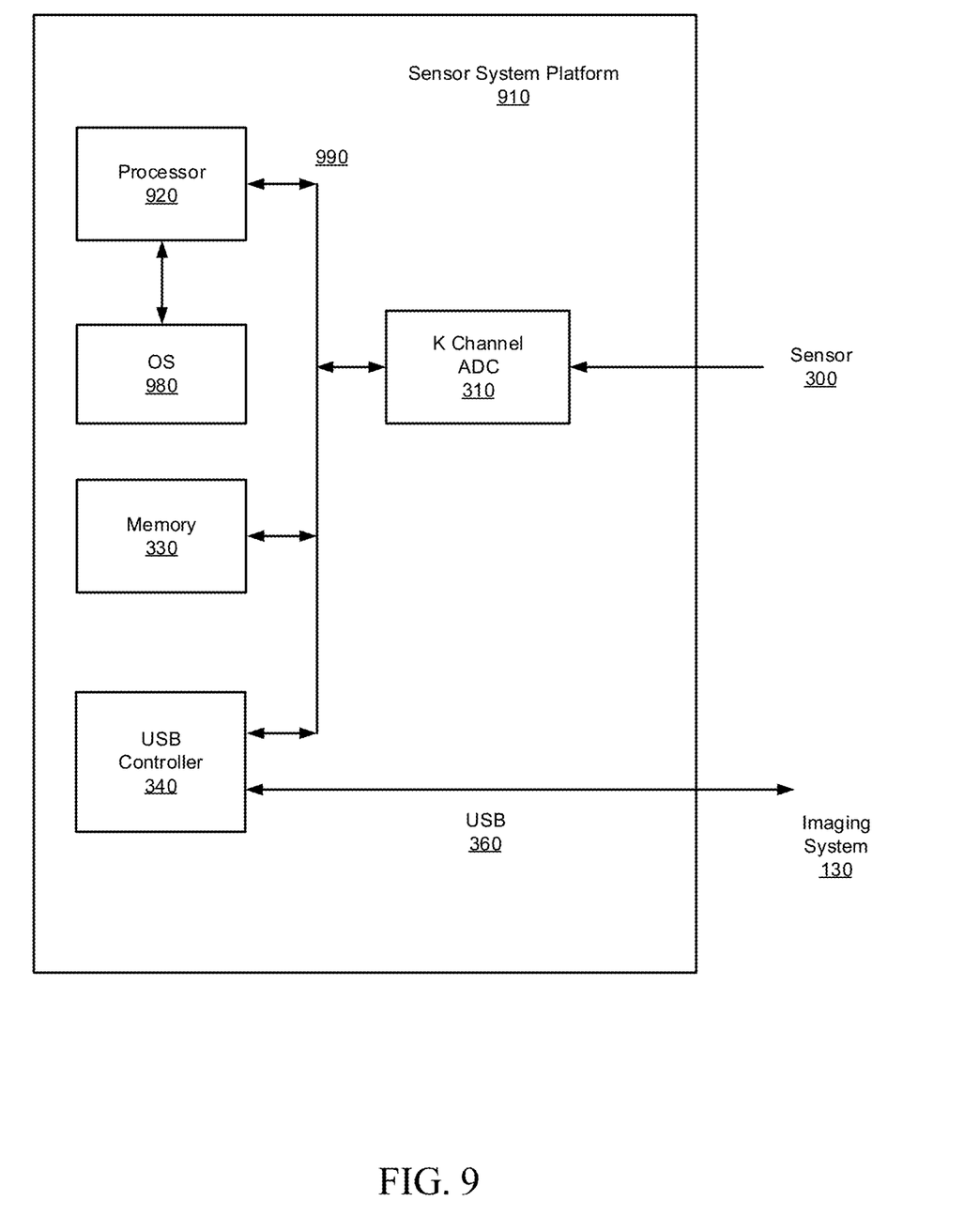
FIG. 9 is a block diagram schematically illustrating a platform for the x-ray sensor system, in accordance with certain embodiments of the present disclosure.

FIG. 9 is a block diagram schematically illustrating a platform for the x-ray sensor system, in accordance with certain embodiments of the present disclosure. In some embodiments, the sensor system platform 910, or portions thereof, may be hosted on, or otherwise be incorporated onto a circuit board configured to fit in a capsule 210, 280 that is suitable for use as an intraoral dental device.

In some embodiments, platform 910 may comprise any combination of a processor 920, a memory 330, a USB controller 340 (or other suitable communication interface), and multichannel ADC 310. As can be further seen, a bus 990 is also provided to allow for communication between the various components listed above and/or other components not shown. Other componentry and functionality not reflected in the block diagram of FIG. 9 will be apparent in light of this disclosure, and it will be appreciated that other embodiments are not limited to any particular hardware configuration.

Processor 920 can be any suitable processor, and may include one or more coprocessors or controllers, such as an audio processor, a graphics processing unit, or hardware accelerator, to assist in control and processing operations associated with sensor system 910. In some embodiments, the processor 920 may be implemented as any number of processor cores. The processor (or processor cores) may be any type of processor, such as, for example, a microprocessor, an embedded processor, a digital signal processor (DSP), a graphics processor (GPU), a network processor, a field programmable gate array or other device configured to execute code. The processors may be multithreaded cores in that they may include more than one hardware thread context (or "logical processor") per core. Processor 920 may be implemented as a complex instruction set computer (CISC) or a reduced instruction set computer (RISC) processor.

Memory 330 can be implemented using any suitable type of digital storage including, for example, flash memory and/or random access memory (RAM). In some embodiments, the memory 330 may include various layers of memory hierarchy and/or memory caches as are known to those of skill in the art. Memory 330 may be implemented as a volatile memory device such as, but not limited to, a RAM, dynamic RAM (DRAM), or static RAM (SRAM) device.

Processor 920 may be configured to execute an Operating System (OS) 980 which may comprise any suitable operating system, such as Google Android (Google Inc., Mountain View, CA), Microsoft Windows (Microsoft Corp., Redmond, WA), Apple OS X (Apple Inc., Cupertino, CA), Linux, or a real-time operating system (RTOS). As will be appreciated in light of this disclosure, the techniques provided herein can be implemented without regard to the particular operating system provided in conjunction with sensor system 910, and therefore may also be implemented using any suitable existing or subsequently-developed systems or platforms.

It will be appreciated that in some embodiments, some of the various components of sensor system 910 may be combined or integrated in a system-on-a-chip (SoC) architecture. In some embodiments, the components may be hardware components, firmware components, software components or any suitable combination of hardware, firmware or software.

Processor 920, which may be implemented as an FPGA in some embodiments, is configured to perform the functions of controller 320, as described previously.

Various embodiments of sensor system 910 may be implemented using hardware elements, software elements, or a combination of both. Examples of hardware elements may include processors, microprocessors, circuits, circuit elements (for example, transistors, resistors, capacitors, inductors, and so forth), integrated circuits, application-specific integrated circuits (ASICs, or other purpose-built semiconductors), programmable logic devices, digital signal processors, field programmable gate arrays (FPGAs), logic gates, registers, semiconductor devices, chips, microchips, chipsets, and so forth. Examples of software may include software components, programs, applications, computer programs, application programs, system programs, machine programs, operating system software, middleware, firmware, software modules, routines, subroutines, functions, methods, procedures, software interfaces, application program interfaces, instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power level, heat tolerances, processing cycle budget, input data rates, output data rates, memory resources, data bus speeds, and other design or performance constraints.

The various embodiments disclosed herein can be implemented in various forms of hardware, software, firmware, and/or special purpose processors. For example, in one embodiment at least one non-transitory computer readable storage medium has instructions encoded thereon that, when executed by one or more processors, causes one or more of the methodologies disclosed herein to be implemented. Other componentry and functionality not reflected in the illustrations will be apparent in light of this disclosure, and it will be appreciated that other embodiments are not limited to any particular hardware or software configuration. Thus, in other embodiments sensor system 910 may comprise additional, fewer, or alternative subcomponents as compared to those included in the example embodiment of FIG. 9.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still cooperate or interact with each other.

The aforementioned non-transitory computer readable medium may be any suitable medium for storing digital information, such as a hard drive, a server, a flash memory, and/or random access memory (RAM), or a combination of memories. In alternative embodiments, the components and/or modules disclosed herein can be implemented with hardware, including gate-level logic such as a field-programmable gate array (FPGA), or alternatively, a purpose-built semiconductor such as an application-specific integrated circuit (ASIC). In some embodiments, the hardware may be modeled or developed using hardware description languages such as, for example Verilog or VHDL. Still other embodiments may be implemented with a microcontroller having a number of input/output ports for receiving and outputting data, and a number of embedded routines for carrying out the various functionalities disclosed herein. It will be apparent that any suitable combination of hardware, software, and firmware can be used, and that other embodiments are not limited to any particular system architecture.

Some examples may be implemented, for example, using a machine-readable medium or article which may store an instruction or a set of instructions that, if executed by a machine, may cause the machine to perform a method and/or operations in accordance with an embodiment provided herein. Such a machine may include, for example, any suitable processing platform, computing platform, computing device, processing device, computing system, processing system, computer, process, or the like, and may be implemented using any suitable combination of hardware and/or software. The machine-readable medium or article may include, for example, any suitable type of memory unit, memory device, memory article, memory medium, storage device, storage article, storage medium, and/or storage unit, such as memory, removable or non-removable media, erasable or non-erasable media, writeable or rewriteable media, digital or analog media, hard disk, floppy disk, compact disk read only memory (CD-ROM), compact disk recordable (CD-R) memory, compact disk rewriteable (CD-RW) memory, optical disk, magnetic media, magneto-optical media, removable memory cards or disks, various types of digital versatile disk (DVD), a tape, a cassette, or the like. The instructions may include any suitable type of code, such as source code, compiled code, interpreted code, executable code, static code, dynamic code, encrypted code, and the like, implemented using any suitable high level, low level, object oriented, visual, compiled, and/or interpreted programming language.

Unless specifically stated otherwise, it may be appreciated that terms such as "processing," "computing," "calculating," "determining," or the like refer to the action and/or process of a computer or computing system, or similar electronic computing device, that manipulates and/or transforms data represented as physical quantities (for example, electronic) within the registers and/or memory units of the computer system into other data similarly represented as physical quantities within the registers, memory units, or other such information storage transmission or displays of the computer system. The embodiments are not limited in this context.

The terms "circuit" or "circuitry," as used in any embodiment herein, are functional structures that include hardware, or a combination of hardware and software, and may comprise, for example, singly or in any combination, hardwired circuitry, programmable circuitry such as computer processors comprising one or more individual instruction processing cores, state machine circuitry, and/or gate level logic. The circuitry may include a processor and/or controller programmed or otherwise configured to execute one or more instructions to perform one or more operations described herein. The instructions may be embodied as, for example, an application, software, firmware, or one or more embedded routines configured to cause the circuitry to perform any of the aforementioned operations. Software may be embodied as a software package, code, instructions, instruction sets and/or data recorded on a computer-readable storage device. Software may be embodied or implemented to include any number of processes, and processes, in turn, may be embodied or implemented to include any number of threads or parallel processes in a hierarchical fashion. Firmware may be embodied as code, instructions or instruction sets and/or data that are hard-coded (e.g., nonvolatile) in memory devices. The circuitry may, collectively or individually, be embodied as circuitry that forms part of a larger system, for example, an integrated circuit (IC), an application-specific integrated circuit (ASIC), a system-on-a-chip (SoC), computers, and other processor-based or functional systems. Other embodiments may be implemented as software executed by a programmable device. In any such hardware cases that include executable software, the terms "circuit" or "circuitry" are intended to include a combination of software and hardware such as a programmable device or a processor capable of executing the software. As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Numerous specific details have been set forth herein to provide a thorough understanding of the embodiments. It will be understood by an ordinarily-skilled artisan, however, that the embodiments may be practiced without these specific details. In other instances, well known operations, components and circuits have not been described in detail so as not to obscure the embodiments. It can be appreciated that the specific structural and functional details disclosed herein may be representative and do not necessarily limit the scope of the embodiments. In addition, although the subject matter has been described in language specific to structural features and/or methodological acts, it is to be understood that the subject matter defined in the appended claims is not necessarily limited to the specific features or acts described herein. Rather, the specific features and acts described herein are disclosed as example forms of implementing the claims.

Further Example Embodiments

The following examples pertain to further embodiments, from which numerous permutations and configurations will be apparent.

One example embodiment of the present disclosure provides an intraoral x-ray sensor system comprising: a pixel circuit associated with each of one or more pixels of an array of pixels and configured to integrate x-ray pulse energy received at the associated pixel, in response to a trigger; a multiplexer configured to readout analog signals from the array of pixels into two or more parallel channels; two or more analog to digital converter (ADC) circuits configured to perform parallel conversion of the analog signals of the channels into digital signals, such that each ADC receives the analog signal of a corresponding one of the parallel channels; a memory; and a controller circuit configured to store the digital signals in the memory as a frame of data.

In some cases, the system further comprises a detection circuit configured to detect the x-ray pulse based on the energy received at the one or more pixels of the array of pixels, and to generate the trigger in response to the detection. In some such cases, the detection circuit is configured to: sum energy received at each of one or more groups of pixels of the array of pixels; enumerate a count of the number of summations that exceed a threshold energy level; and detect the x-ray pulse in response to the count exceeding a threshold count value. In some such cases, the groups of pixels are distributed over two or more rows of the array of pixels. In some such cases, the two or more rows are irregularly spaced. In some cases, the system further comprises a Universal Serial Bus (USB) controller configured to transmit the frame of data from the memory, over a Universal Serial Bus (USB), to an imaging system. In some such cases, the x-ray pulse is a first x-ray pulse, and the USB controller is configured to transmit the frame of data over the USB while the sensor system processes a second x-ray pulse. In some cases, the pixel circuit is configured to adjust a gain value for each of the pixels of the array of pixels.

Another example embodiment of the present disclosure provides a computer program product including one or more non-transitory machine-readable mediums encoded with instructions that when executed by one or more processors cause a process to be carried out for intraoral x-ray sensing, the process comprising: integrating x-ray pulse energy received at each of one or more pixels of an array of pixels, in response to a trigger; multiplexing readout of analog signals from the array of pixels into two or more parallel channels; performing parallel conversion of the analog signals of the channels into digital signals; and storing the digital signals in memory as a frame of data.

In some cases, the process further comprises detecting the x-ray pulse based on the energy received at the one or more pixels of the array of pixels and generating the trigger in response to the detection. In some such cases, the process of detecting the x-ray pulse comprises: summing energy received at each of one or more groups of pixels of the array of pixels; enumerating a count of the number of summations that exceed a threshold energy level; and detecting the x-ray pulse in response to the count exceeding a threshold count value. In some such cases, the groups of pixels are distributed over two or more rows of the array of pixels. In some cases, the process further comprises transmitting the frame of data from the memory, over a Universal Serial Bus (USB), to an imaging system. In some such cases, the x-ray pulse is a first x-ray pulse, and the process further comprises transmitting the frame of data over the USB while performing processing associated with a second x-ray pulse.

Another example embodiment of the present disclosure provides a method for intraoral x-ray sensing, the method comprising: integrating, by a processor-based system, x-ray pulse energy received at each of one or more pixels of an array of pixels, in response to a trigger; multiplexing, by the processor-based system, readout of analog signals from the array of pixels into two or more parallel channels; performing, by the processor-based system, parallel conversion of the analog signals of the channels into digital signals; and storing, by the processor-based system, the digital signals in memory as a frame of data.

In some cases, the method further comprises detecting the x-ray pulse based on the energy received at the one or more pixels of the array of pixels and generating the trigger in response to the detection. In some such cases, the detecting of the x-ray pulse comprises: summing energy received at each of one or more groups of pixels of the array of pixels; enumerating a count of the number of summations that exceed a threshold energy level; and detecting the x-ray pulse in response to the count exceeding a threshold count value. In some such cases, the groups of pixels are distributed over two or more rows of the array of pixels. In some cases, the method further comprises transmitting the frame of data from the memory, over a Universal Serial Bus (USB), to an imaging system. In some such cases, the x-ray pulse is a first x-ray pulse, and the method further comprises transmitting the frame of data over the USB while performing processing associated with a second x-ray pulse.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents. Various features, aspects, and embodiments have been described herein. The features, aspects, and embodiments are susceptible to combination with one another as well as to variation and modification, as will be understood by those having skill in the art. The present disclosure should, therefore, be considered to encompass such combinations, variations, and modifications. It is intended that the scope of the present disclosure be limited not by this detailed description, but rather by the claims appended hereto. Future filed applications claiming priority to this application may claim the disclosed subject matter in a different manner and may generally include any set of one or more elements as variously disclosed or otherwise demonstrated herein.

What is claimed is:

1. An intraoral x-ray sensor system comprising:
a pixel circuit associated with each of one or more pixels of an array of pixels and configured to integrate x-ray pulse energy received at the associated pixel, in response to a trigger;
a multiplexer configured to readout analog signals from the array of pixels into two or more parallel channels;
two or more analog to digital converter (ADC) circuits configured to perform parallel conversion of the analog signals of the channels into digital signals, such that each ADC receives the analog signal of a corresponding one of the parallel channels;
a memory; and
a controller circuit configured to store the digital signals in the memory as a frame of data.

2. The sensor system of claim 1, further comprising a detection circuit configured to detect the x-ray pulse based on the energy received at the one or more pixels of the array of pixels, and to generate the trigger in response to the detection.

3. The sensor system of claim 2, wherein the detection circuit is configured to:
sum energy received at each of one or more groups of pixels of the array of pixels;
enumerate a count of the number of summations that exceed a threshold energy level; and
detect the x-ray pulse in response to the count exceeding a threshold count value.

4. The sensor system of claim 3, wherein the groups of pixels are distributed over two or more rows of the array of pixels.

5. The sensor system of claim 4, wherein the two or more rows are irregularly spaced.

6. The sensor system of claim 1, further comprising a Universal Serial Bus (USB) controller configured to transmit the frame of data from the memory, over a Universal Serial Bus (USB), to an imaging system.

7. The sensor system of claim 5, wherein the x-ray pulse is a first x-ray pulse, and the USB controller is configured to transmit the frame of data over the USB while the sensor system processes a second x-ray pulse.

8. The sensor system of claim 1, wherein the pixel circuit is configured to adjust a gain value for each of the pixels of the array of pixels.

9. A computer program product including one or more non-transitory machine-readable mediums encoded with instructions that when executed by one or more processors cause a process to be carried out for intraoral x-ray sensing, the process comprising:
integrating x-ray pulse energy received at each of one or more pixels of an array of pixels, in response to a trigger;
multiplexing readout of analog signals from the array of pixels into two or more parallel channels;
performing parallel conversion of the analog signals of the channels into digital signals, wherein two or more analog to digital converters (ADC) perform the parallel conversion of the analog signals into digital signals, such that each ADC receives the analog signal or a corresponding one of the parallel channels; and
storing the digital signals in memory as a frame of data.

10. The computer program product of claim 9, wherein the process further comprises detecting the x-ray pulse based on the energy received at the one or more pixels of the array of pixels and generating the trigger in response to the detection.

11. The computer program product of claim 10, wherein the process of detecting the x-ray pulse comprises:
summing energy received at each of one or more groups of pixels of the array of pixels;
enumerating a count of the number of summations that exceed a threshold energy level; and
detecting the x-ray pulse in response to the count exceeding a threshold count value.

12. The computer program product of claim 11, wherein the groups of pixels are distributed over two or more rows of the array of pixels.

13. The computer program product of claim 9, wherein the process further comprises transmitting the frame of data from the memory, over a Universal Serial Bus (USB), to an imaging system.

14. The computer program product of claim 13, wherein the x-ray pulse is a first x-ray pulse, and the process further comprises transmitting the frame of data over the USB while performing processing associated with a second x-ray pulse.

15. A method for intraoral x-ray sensing, the method comprising:
integrating, by a processor-based system, x-ray pulse energy received at each of one or more pixels of an array of pixels, in response to a trigger;

multiplexing, by the processor-based system, readout of analog signals from the array of pixels into two or more parallel channels;

performing, by the processor-based system, parallel conversion of the analog signals of the channels into digital signals, wherein two or more analog to digital converters (ADC) perform the parallel conversion of the analog signals into digital signals, such that each ADC receives the analog signal or a corresponding one of the parallel channels; and storing, by the processor-based system, the digital signals in memory as a frame of data.

16. The method of claim 15, further comprising detecting the x-ray pulse based on the energy received at the one or more pixels of the array of pixels and generating the trigger in response to the detection.

17. The method of claim 16, wherein the detecting of the x-ray pulse comprises:

summing energy received at each of one or more groups of pixels of the array of pixels;

enumerating a count of the number of summations that exceed a threshold energy level; and detecting the x-ray pulse in response to the count exceeding a threshold count value.

18. The method of claim 17, wherein the groups of pixels are distributed over two or more rows of the array of pixels.

19. The method of claim 15, further comprising transmitting the frame of data from the memory, over a Universal Serial Bus (USB), to an imaging system.

20. The method of claim 19, wherein the x-ray pulse is a first x-ray pulse, and the method further comprises transmitting the frame of data over the USB while performing processing associated with a second x-ray pulse.

* * * * *